US005809998A

United States Patent [19]

Hughes et al.

[11] Patent Number: 5,809,998

[45] Date of Patent: Sep. 22, 1998

[54] INSULATION JACKET FOR BREATHING GAS DEVICE

[75] Inventors: Robert Hughes, Lynn Haven; Billy Courson; Joseph Rudolph, both of Panama City Beach, all of Fla.

[73] Assignee: The United States of America as represented by the Secretary of the Navy, Washington, D.C.

[21] Appl. No.: 695,845

[22] Filed: Aug. 8, 1996

[51] Int. Cl.[6] .................................................. A61M 15/00

[52] U.S. Cl. .................................. 128/204.17; 128/200.24

[58] Field of Search ......................... 128/200.24, 201.13, 128/201.21, 204.17, 205.22, 206.27, DIG. 15; 220/460, 903

[56] References Cited

U.S. PATENT DOCUMENTS

| | | | |
|---|---|---|---|
| 1,700,615 | 1/1929 | O'Brien | 220/460 |
| 1,727,530 | 9/1929 | Washburn | 220/460 |
| 2,365,086 | 12/1944 | Kamowski | 220/460 |
| 2,838,085 | 6/1958 | Beeler | 220/460 |
| 3,133,422 | 5/1964 | Paivanas et al. | 220/460 |
| 3,906,129 | 9/1975 | Damois | 220/460 |
| 4,181,126 | 1/1980 | Hendry | 128/205.22 |
| 4,197,890 | 4/1980 | Simko | 220/903 |
| 4,438,764 | 3/1984 | Eppolito | 128/205.22 |
| 4,996,982 | 3/1991 | Williamson | 128/206.27 |
| 5,036,845 | 8/1991 | Scholley | 128/205.22 |
| 5,188,267 | 2/1993 | Sargent et al. | 128/205.22 |
| 5,188,981 | 2/1993 | Stiles et al. | 428/195 |
| 5,259,372 | 11/1993 | Gross et al. | 128/204.18 |
| 5,308,571 | 5/1994 | Stiles et al. | 264/257 |
| 5,318,821 | 6/1994 | Bradley, Jr. | 220/460 |
| 5,609,265 | 3/1997 | Haberkorn et al. | 220/903 |

*Primary Examiner*—Aaron J. Lewis
*Attorney, Agent, or Firm*—Harvey A. Gilbert; Kenneth W. Dobyns

[57] ABSTRACT

An insulation jacket is provided for a breathing gas device. A first jacket portion wraps completely about the device's cylinder and gas delivery valve. A second jacket portion wraps about a high-pressure regulator coupled in-line with the gas delivery valve and a plurality of gas delivery conduits extending from the high-pressure regulator. The first and second jacket portions are formed from a flexible insulating material of laminate construction. A plurality of fastening strips, e.g., hook-and-loop fastening strips, cooperate with first and second jacket portions after they are wrapped about the respective portions of the breathing gas device.

12 Claims, 3 Drawing Sheets

INSULATION JACKET FOR BREATHING GAS DEVICE

ORIGIN OF THE INVENTION

The invention described herein was made in the performance of official duties by employees of the Department of the Navy and may be manufactured, used, licensed by or for the Government for any governmental purpose without payment of any royalties thereon.

FIELD OF THE INVENTION

The invention relates generally to breathing gas devices, and more particularly to an insulation jacket for a breathing gas device that reduces heat transfer to the breathing gas from a high-temperature operating environment.

BACKGROUND OF THE INVENTION

Breathing gas devices are used for a variety of hazardous situations, e.g., fire-fighting, hazardous material (hazmat) handling or disasters, chemical warfare, etc. The elevated temperatures encountered in these various situations tend to heat the breathing gas in these devices to levels that can cause psychological stress, e.g., claustrophobia, physical injury or even death. However, conventional (open-circuit) breathing gas devices are not optimized to reduce or minimize heat gains. Safe operation relies on the premise that fire fighters will exit the fire due to heat stress or loss of breathing gas when appropriate. In hazmat or chemical warfare situations, personnel may not have the opportunity to exit a contaminated area quickly due to decontamination or other safety procedures.

Existing cooling schemes for high-temperature operation generally consist of using ice packs in a chest vest to provide core temperature cooling. However, the use of ice packs on navy ships is undesirable because ice may not be available during damage control situations. Additionally, open-circuit breathing apparatus utilize the expansion of the high pressure breathing air to provide cool breathing gas to the user. However, because these devices are not thermally optimized for operation in high temperatures, a majority of the gas-expansion cooling effect is lost to the high-temperature surroundings.

SUMMARY OF THE INVENTION

Accordingly, it is an object of the present invention to provide an apparatus to reduce the amount of heat transferred from a high-temperature environment to the breathing gas of a breathing gas device.

Another object of the present invention is to provide an apparatus that can be readily used with conventional breathing gas devices to reduce heat transfer to the device's breathing gas from a high-temperature environment.

Still another object of the present invention is to provide an apparatus for reducing heat transfer to a breathing gas device's breathing gas without requiring the use of ice or other material requiring cold storage.

Other objects and advantages of the present invention will become more obvious hereinafter in the specification and drawings.

In accordance with the present invention, an insulation jacket is provided for a breathing gas device. A first jacket portion insulates a cylinder containing breathing gas and a gas delivery valve cooperating with and depending from a first end of the cylinder. The first jacket portion is formed from flexible material having insulating properties. The first jacket portion has a rectangular body portion and a round body portion depending from an edge of the rectangular body portion. The rectangular body portion wraps completely about the cylinder and extends beyond the gas delivery valve such that rectangular body portion can wrap about the gas delivery valve. The round body portion covers a second end of the cylinder so wrapped with the rectangular body portion. A second jacket portion insulates a high-pressure regulator coupled in-line with the gas delivery valve and a plurality of gas delivery conduits extending from the high-pressure regulator. The second jacket portion is also formed from the flexible material and has a main body portion with branches extending away from the main body portion. The main body portion wraps completely about the high-pressure regulator. Each branch wraps completely around one of the gas delivery conduits. A plurality of fastening strips, e.g., hook-and-loop fastening strips, cooperate with first and second jacket portions after they are wrapped about the respective portions of the breathing gas device.

DETAILED DESCRIPTION OF THE INVENTION

Figure 1:
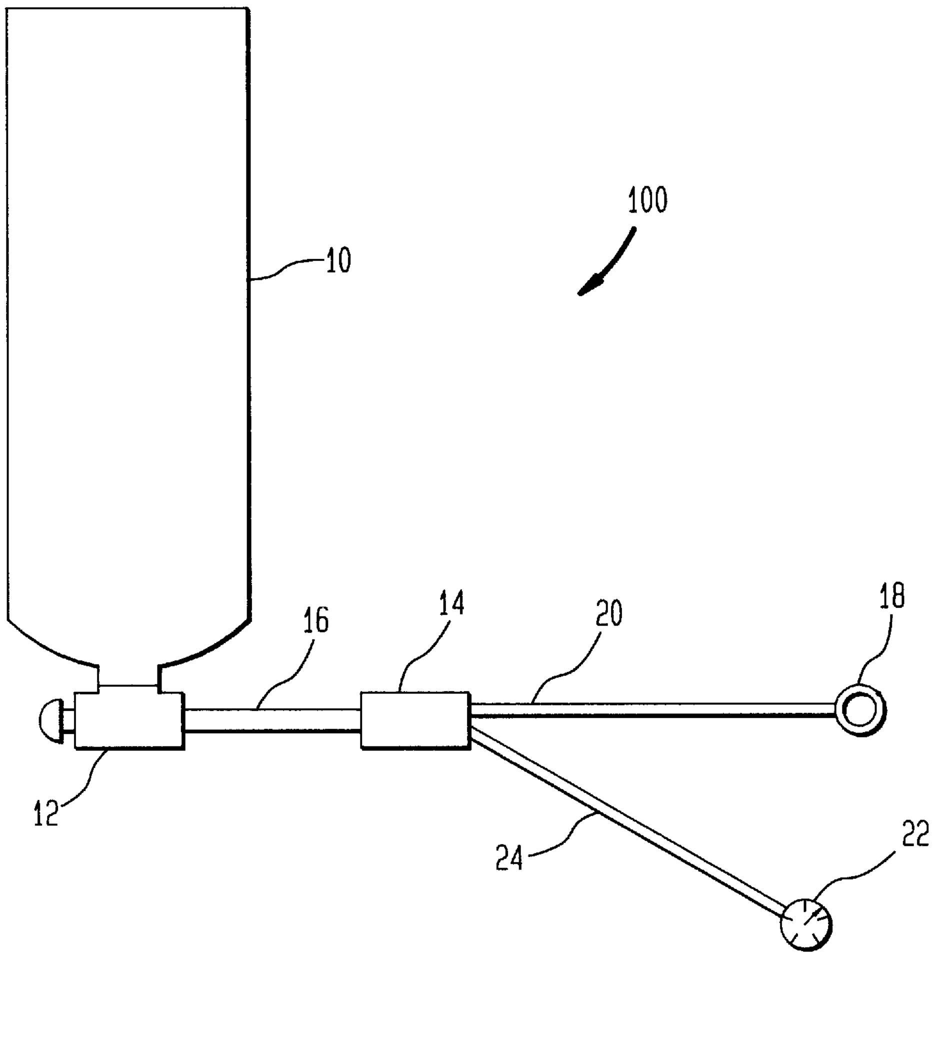
FIG. 1 is a side view of a conventional, open-circuit breathing gas device that is to be insulated by the present invention.

Referring now to the drawings, and more particularly to FIG. 1, a conventional open-circuit breathing gas device is shown and referenced generally by numeral 100. While the present invention can also be used with the inhalation side of closed-circuit breathing gas devices, the present invention will be described herein by way of example for use with open-circuit breathing gas device 100. One example of such a breathing gas device is the "Sigma" available from Survivair Corporation, Santa Ana, Calif.

Breathing gas device 100 stores a breathing gas under high pressure within cylinder 10. Gas delivery valve 12 depends from one end of cylinder 10 and communicates with the gas in cylinder 10. Valve 12 is connected to high-pressure regulator 14 via high-pressure hose 16. High-pressure regulator 14 is connected to low-pressure regulator 18 via conduit 20 and to pressure gauge 22 via conduit 24. Low-pressure regulator 18 connects to a facemask (not shown) that supplies the breathing gas to a user.

When valve 12 is opened, high-pressure breathing gas flows to high-pressure regulator 14 through high-pressure hose 16. The highly pressurized breathing gas is passed to pressure gauge 22 via conduit 24. High-pressure regulator 14 also reduces the pressure of the breathing gas that is passed to low pressure regulator 18 via conduit 20.

Figure 2:
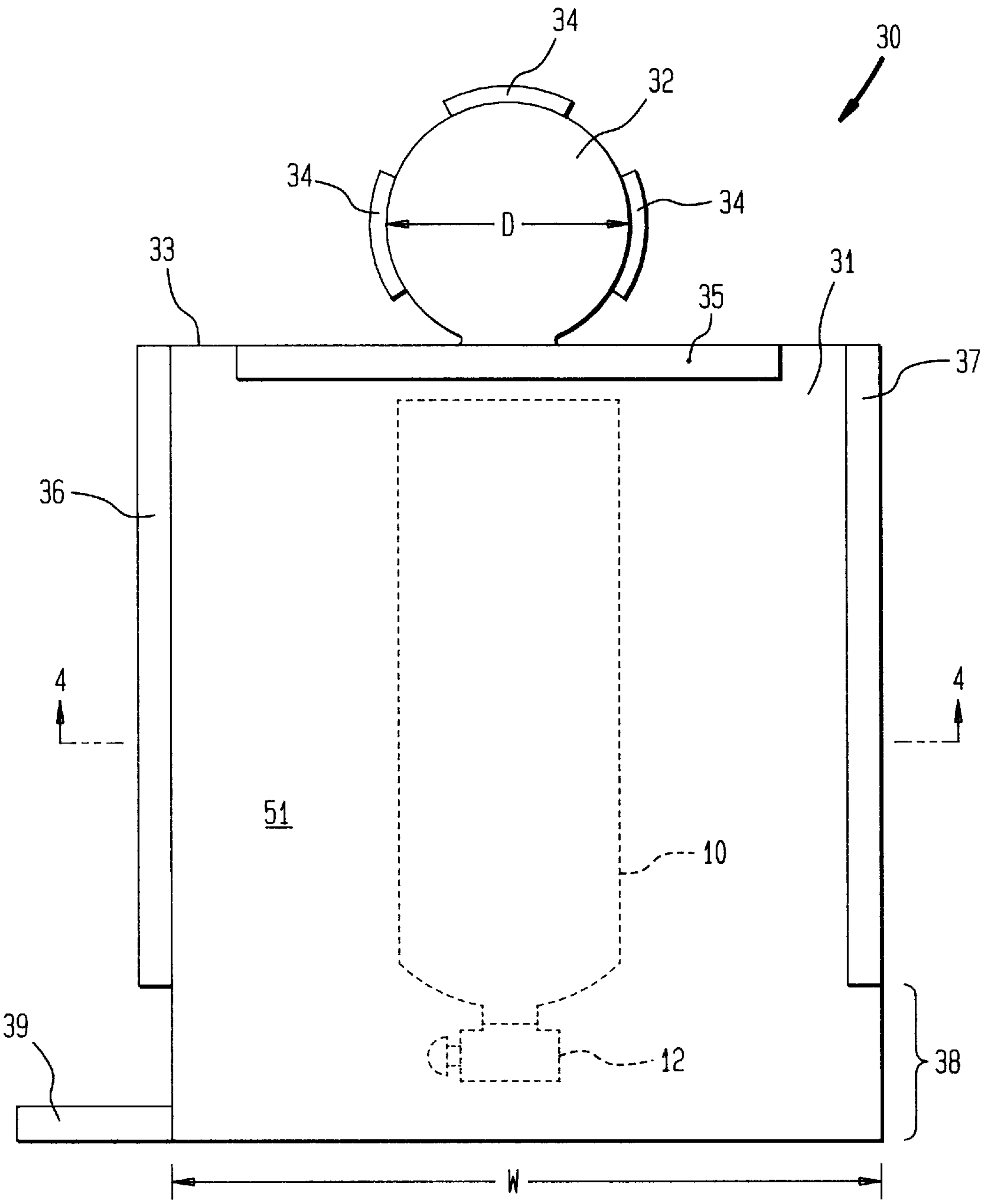
FIG. 2 is a plan view of the first portion of an insulation jacket according to a preferred embodiment of the present invention that thermally insulates the gas cylinder of the breathing gas device.
Figure 3:
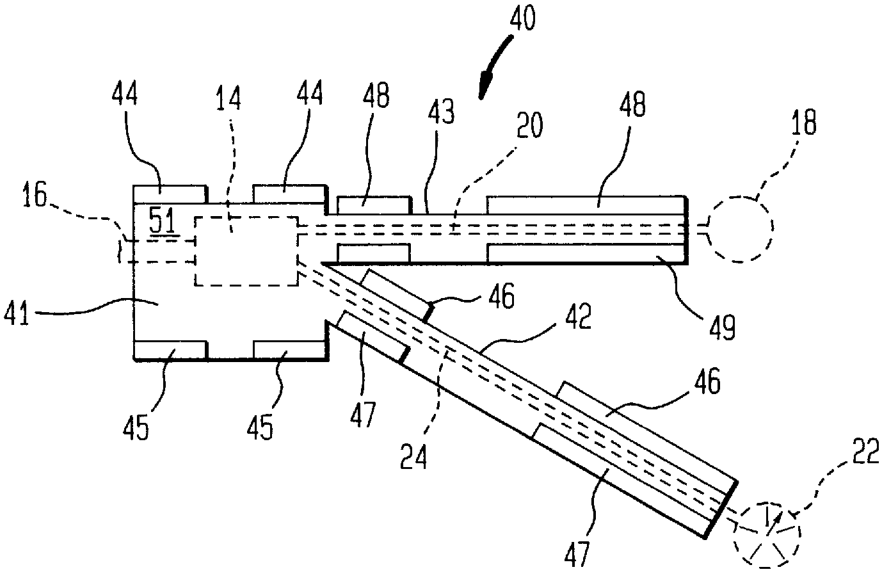
FIG. 3 is a plan view of the second portion of the insulation jacket according to the preferred embodiment of the present invention that thermally insulates the gas delivery system of the breathing gas device.

The insulation jacket of the present invention is shown in plan view in FIGS. 2 and 3. The portion of the jacket that insulates cylinder 10 and valve 12 (shown in phantom dashed-line form) is shown in FIG. 2 and is referenced generally by reference numeral 30. The portion of the jacket that insulates high-pressure regulator 14, hose 16, and conduits 20 and 24 (shown in phantom, dashed-line form) is shown in FIG. 3 and is referenced generally by reference numeral 40. Although conduit 24 does not transport breathing gas to the user, conduit 24 can still serve as a source of heat transfer to the gas and is therefore insulated by jacket portion 40. Both jacket portions 30 and 40 are made from a flexible insulating material that is non-flammable and/or inert with respect to the intended operating environment.

Figure 4:
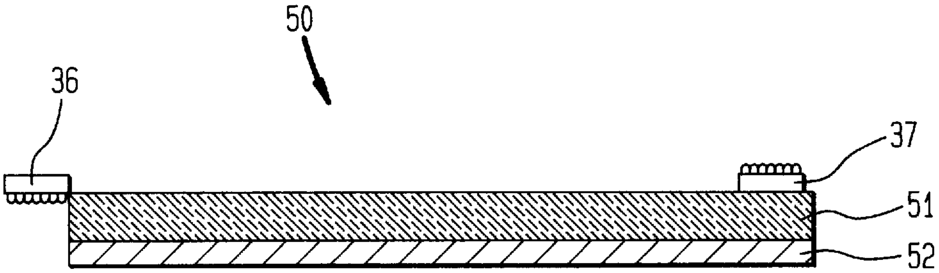
FIG. 4 is a cross-sectional view taken along line 4—4 of FIG. 2 showing the laminate construction of the material used to fabricate the insulation jacket of the present invention.

In the preferred embodiment jacket portions 30 and 40 are of laminate construction. For example, a two-layer laminate construction is shown in cross-section in FIG. 4 where layer 51 is an insulating material, e.g., silicone foam, and layer 52 is an thermally reflective material, e.g., an aluminized fabric. One such laminate is available commercially from Bisco Products, Elk Grove Village, Ill., under the trademark EXOBLOC.

Jacket portions 30 and 40 are wrapped about the respective portions of device 100 such that insulating layer 51 faces device 100 while thermally reflective layer 52 faces ambient air. In this way, thermally reflective layer 52 acts as a radiant heat shield and can protect insulating layer 51 from moisture damage.

Jacket portion 30 is typically cut from a single piece of material 50 and includes rectangular portion 31 and round portion 32. Rectangular portion 31 has a width W sufficient to be wrapped completely about the circumference of cylinder 10. For reasons that will become apparent, the length L of rectangular portion 31 must be longer than the length of cylinder 10 and valve 12. Depending from width-wise edge 33 of rectangular portion 31 is round portion 32 having a diameter D commensurate with the diameter of cylinder 10.

In use, jacket portion 30 is wrapped about cylinder 10 and valve 12 of device 100. Accordingly, means must be provided to keep jacket portion 30 so wrapped. One way of accomplishing this is to attach (e.g., stitch with nylon thread or glue) a plurality of hook-and-loop fastener strips to jacket portion 30. Hook strips 34 on round portion 32 cooperate with loop strip 35 on width-wise edge 33 when rectangular portion 31 is wrapped about cylinder 10. To maintain rectangular portion 31 in its wrapped configuration, hook strip 36 and loop strip 37 are attached along either lengthwise edge of rectangular portion 31. Note that these strips 36 and 37 extend from width-wise edge 33, i.e., the sealed end of cylinder 10, for the length of cylinder 10. The remaining portion of rectangular portion 31, designated extension portion 38, is wrapped about valve 12 and maintained in place by use of hook-and-loop fastening strip 39. By shaping extension portion in this general fashion, jacket portion 30 can be used with a variety of designs of valve 12.

Jacket portion 40 is similarly cut from a single piece of material 50 and includes a base or main portion 41 and first and second branch portions 42 and 43, respectively. In use, main portion 41 is wrapped completely about high-pressure hose 16 and regulator 14. First branch portion 42 is wrapped completely about conduit 24 and second branch portion 43 is wrapped completely about conduit 20. A plurality of hook-and-loop fastener strips are provided about the periphery of jacket portion 40 to hold it in the wrapped configuration. More specifically, hook strips 44 cooperate with loop strips 45 on main portion 41; hook strips 46 cooperate with loop strips 47 on first branch portion 42; and hook strips 48 cooperate with loop strips 49 on second branch portion 43. Note that the plurality of hook-and-loop fastening strips are attached such that only thermally reflective layer 52 is exposed to ambient air when jacket portions 30 and 40 are wrapped on device 100. However, should any of the fastening strips be exposed, they can be covered a thermally reflective material.

The advantages of the present invention are numerous. The insulation jacket greatly reduces heat transfer from a high-temperature environment to the breathing gas of a breathing gas device. Tests of a breathing gas device equipped with the present invention (in high-temperature environments of 250° F.) have produced face mask temperature reductions of 50° F. or more when compared with a breathing gas device that is not equipped with the insulation jacket. The present invention does not require ice or any special storage prior to its use. The insulating material need not be charged prior to use. Thus, the present invention will be of great use in any situation where breathing gas devices are required.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. An insulation jacket for a breathing gas device, comprising:

a first jacket portion for insulating a cylinder containing breathing gas and a gas delivery valve cooperating with and depending from a first end of a cylinder, said first jacket portion formed from flexible material having insulating properties, said first jacket portion having a rectangular body portion and a round body portion depending from an edge of said rectangular body portion, said rectangular body portion for wrapping completely about a cylinder and extending beyond a gas delivery valve such that said rectangular body portion can wrap about a gas delivery valve, said round body portion for covering a second end of a cylinder so wrapped with said rectangular body portion;

a second jacket portion for insulating i) a high-pressure regulator coupled in-line with a gas delivery valve and ii) a plurality of gas delivery conduits extending from a high-pressure regulator, said second jacket portion formed from said flexible material and having a main body portion with a plurality of branches extending away from said main body portion in correspondence with a plurality of gas conduits, said main body portion for wrapping completely about a high-pressure regulator and each of said plurality of branches for wrapping completely around one of a plurality of gas delivery conduits; and means cooperating with said first jacket portion for maintaining said first jacket portion so wrapped about a cylinder and a gas delivery valve, and cooperating with said second jacket portion for maintaining said second jacket portion so wrapped about a high-pressure regulator and a plurality of gas delivery conduits.

2. An insulation jacket as in claim 1 wherein said flexible material is a laminate having an insulation layer and a thermally reflective layer, wherein said thermally reflective layer is exposed to ambient air when said first jacket portion and said second jacket portion are so wrapped about a breathing gas device.

3. An insulation jacket as in claim 2 wherein said insulation layer comprises a silicone foam.

4. An insulation jacket as in claim 2 wherein said thermally reflective layer is an aluminized fabric.

5. An insulation jacket as in claim 1 wherein said means cooperating with said first jacket portion and said second jacket portion comprises a plurality of hook-and-loop fastener strips.

6. An insulation jacket as in claim 5 wherein said plurality of hook-and-loop fastener strips are attached about the edges of said first jacket portion and said second jacket portion.

7. An insulation jacket for a breathing gas device, comprising:

a first jacket portion formed from flexible material having insulating properties, said first jacket portion having a rectangular body portion and a round body portion depending from an edge of said rectangular body portion;

a second jacket portion formed from said flexible material and having a main body portion with a plurality of branches extending away from said main body portion;

first fasteners cooperating with said first jacket portion for maintaining said first jacket portion in a wrapped configuration about a cylinder and a gas delivery valve of a breathing gas device; and second fasteners cooperating with said second jacket portion for maintaining said main body portion of said second jacket portion in a wrapped configuration about a high-pressure regulator of a breathing gas device, and for maintaining each of said plurality of branches in a wrapped configuration about one of a plurality of gas delivery conduits extending from a high-pressure regulator of a breathing device.

8. An insulation jacket as in claim 7 wherein said flexible material is a laminate having an insulation layer and a thermally reflective layer, wherein said thermally reflective layer is exposed to ambient air when said first jacket portion and said second jacket portion are so maintained in respective ones of said wrapped configurations.

9. An insulation jacket as in claim 8 wherein said insulation layer comprises a silicone foam.

10. An insulation jacket as in claim 8 wherein said thermally reflective layer is an aluminized fabric.

11. An insulation jacket as in claim 7 wherein said first fasteners and said second fasteners comprise a first plurality of hook-and-loop fastener strips and a second plurality of hook-and-loop fastener strips, respectively.

12. An insulation jacket as in claim 11 wherein said first plurality of hook-and-loop fastener strips are attached about the edges of said first jacket portion, and wherein said second plurality of hook-and-loop fastener strips are attached about the edges of said second jacket portion.

* * * * *